United States Patent
Bhaduri et al.

(10) Patent No.: US 11,710,048 B2
(45) Date of Patent: Jul. 25, 2023

(54) METHOD AND DEVICE FOR ASSESSING FEASIBILITY OF BIOCHEMICAL REACTION IN ORGANISM

(71) Applicant: Samsung Electronics Co., Ltd, Suwon-si (KR)

(72) Inventors: Anirban Bhaduri, Bangalore (IN); Tadi Venkata Siva Kumar, Bangalore (IN); Taeyong Kim, Daejeon (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 1641 days.

(21) Appl. No.: 15/639,724

(22) Filed: Jun. 30, 2017

(65) Prior Publication Data

US 2018/0012129 A1    Jan. 11, 2018

(30) Foreign Application Priority Data

Jul. 5, 2016   (IN) .............................. 201641023142
Sep. 2, 2016   (KR) ........................ 10-2016-0113276

(51) Int. Cl.
*G06N 5/022*   (2023.01)
*G16B 5/00*   (2019.01)
*G16C 20/10*   (2019.01)
*G16B 5/20*   (2019.01)
*G06N 5/04*   (2023.01)

(52) U.S. Cl.
CPC ............... *G06N 5/022* (2013.01); *G16B 5/00* (2019.02); *G16B 5/20* (2019.02); *G16C 20/10* (2019.02); *G06N 5/04* (2013.01)

(58) Field of Classification Search
None
See application file for complete search history.

(56) References Cited

U.S. PATENT DOCUMENTS

| | | | |
|---|---|---|---|
| 9,026,373 B2 | 5/2015 | Zhou et al. | |
| 10,510,434 B2 | 12/2019 | Siva Kumar et al. | |
| 2006/0052942 A1 | 3/2006 | Hsu et al. | |
| 2016/0024689 A1 | 1/2016 | Dana et al. | |
| 2016/0103979 A1 | 4/2016 | Giri et al. | |
| 2016/0162632 A1 | 6/2016 | Yun et al. | |

FOREIGN PATENT DOCUMENTS

| | | |
|---|---|---|
| JP | 2014-501097 A | 1/2014 |
| KR | 0655495 B1 | 12/2006 |
| KR | 1020160012061 A | 2/2016 |

OTHER PUBLICATIONS

A. Cho et al., Prediction of novel synthetic pathways for the production of desired chemicals, BMC Syst. Biol. vol. 4, 35 (2010), 16 pp.
English Translation of Office Action dated Jul. 4, 2022 issued in KR Patent Application No. 10-2016-0113276, 6 pp.
Office Action dated Jul. 4, 2022 issued in KR Patent Application No. 10-2016-0113276, 37 pp.
Hamdalla et al., Metabolic Pathway Predictions for Metabolomics: A Molecular Structure Matching Approach, *Journal of Chemical Information and Modeling*, 55: 709-718 (2015).

*Primary Examiner* — G Steven Vanni
(74) *Attorney, Agent, or Firm* — Cantor Colburn LLP (57) ABSTRACT

Provided are a method and device for assessing a feasibility of one or more biochemical reactions in an organism. The method includes receiving an input representing the organism and input representing one or more biochemical reactions that are to be assessed; computing a reaction feasibility score for each of the one or more input biochemical reactions a knowledgebase; and selecting the biochemical reaction that is likely to occur in the organism.

14 Claims, 5 Drawing Sheets

METHOD AND DEVICE FOR ASSESSING FEASIBILITY OF BIOCHEMICAL REACTION IN ORGANISM

CROSS-REFERENCE TO RELATED APPLICATIONS

This application claims the benefit of Indian Patent Application No. 201641023142, filed on Jul. 5, 2016, in the Indian Patent Office, and Korean Patent Application No. 10-2016-0113276, filed on Sep. 2, 2016, in the Korean Intellectual Property Office, the disclosures of which are incorporated herein in their entireties by reference.

BACKGROUND

1. Field

The present disclosure relates to a synthetic reaction obtained through metabolic engineering, and more particularly to a method of assessing a feasibility of a biochemical reaction in an organism.

2. Description of the Related Art

Metabolic engineering provides an environment-friendly alternative to chemical processing. Metabolic engineering is performed via one or more biochemical reactions in an organism. The success of metabolic engineering depends on the feasibility and efficiency of a biochemical reaction in the organism. The efficiency of the biochemical reaction in the organism depends on the nature of the chemical reaction that is artificially engineered and the ease of biochemical conversion in the organism. These two parameters depend on a host which engineers the reaction. Therefore, in metabolic engineering, it is very important to select an appropriate host organism for engineering a reaction.

SUMMARY

Provided are methods and devices for assessing a feasibility of a biochemical reaction in an organism.

Additional aspects will be set forth in part in the description which follows and, in part, will be apparent from the description, or may be learned by practice of the presented embodiments.

According to an aspect of an embodiment, a method of assessing a feasibility of one or more input biochemical reactions in an organism includes: receiving an input representing the organism and input representing one or more biochemical reactions that are to be assessed; computing a reaction feasibility score for each of the one or more input biochemical reactions a knowledge base; and selecting the biochemical reaction that is to occur in the organism, based on the computed reaction feasibility score. The method may also include sorting the one or more input biochemical reactions, based on the computed reaction feasibility score.

According to an aspect of another embodiment, a non-transitory computer-readable recording medium has recorded thereon a computer program for executing the method of assessing a feasibility of a biochemical reaction in an organism.

According to an aspect of another embodiment, a device for assessing a feasibility of one or more input biochemical reactions in an organism includes: a processor configured to receive an input representing the organism and input representing one or more biochemical reactions that are to be assessed, compute a reaction feasibility score for each of the one or more input biochemical reactions, based on a knowledge base, sort the one or more biochemical reactions that are input, based on the computed reaction feasibility score, and select the biochemical reaction that is to occur in the organism, based on the computed reaction feasibility score; and a memory connected to the processor.

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Most of the terms used herein are general terms that have been widely used in the technical art to which the present inventive concepts pertain. However, some of the terms used herein may be created reflecting intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present inventive concept.

Throughout the specification, it will be understood that when an element is referred to as being "connected" to another element, it may be "directly connected" to the other element or "connected" to the other element with intervening elements therebetween. It will be further understood that when a part "includes" or "comprises" an element, unless otherwise defined, the part may further include other elements, not excluding the other elements.

It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

The example embodiments of the present disclosure will now be described in detail with reference to the accompanying drawings. However, the present inventive concepts are not limited to the example embodiments. The inventive concepts can be modified in various forms. Thus, the example embodiments of the present inventive concepts are only provided to explain more clearly the present inventive concepts to the person of ordinary skill in the art. In the accompanying drawings, like reference numerals are used to indicate like components. As used herein, the term "and/or" includes any and all combinations of one or more of the associated listed items.

The present disclosure provides a method of assessing a feasibility of a biochemical reaction in an organism. As a result, one or more biochemical reactions which may be efficiently processed in a given organism to deliver a desired outcome may be identified. Alternatively, from among given organisms, the most suitable organism, in which a given set of biochemical reactions may be efficiently carried out, may be selected. The method according to the present disclosure may be performed as an in-silico method to analyze related data, thereby making the whole process fast, efficient, and accurate.

The method according to the present disclosure may take into account biochemical natures or attributes of organisms along with chemical characteristics of the biochemical reactions that are to be assessed. These attributes may enhance the accuracy of the selection process.

The present disclosure provides a method of assessing a feasibility of a biochemical reaction in an organism, according to an example embodiment. The assessment includes computing a reaction feasibility score for the biochemical reaction with reference to a knowledge base, while considering parameters of (a) a similarity distance between biochemical reactions and a reference reaction available in the knowledge base, the reference reaction being closest to the biochemical reaction that is to be assessed and related to the nativity of the biochemical reaction to help identify the reaction; and (b) transformation probabilities of transformations, which are attributed to the biochemical reaction and signify the frequency of the occurrence of transformations associated with the biochemical reactions in the knowledge base.

Figure 6:
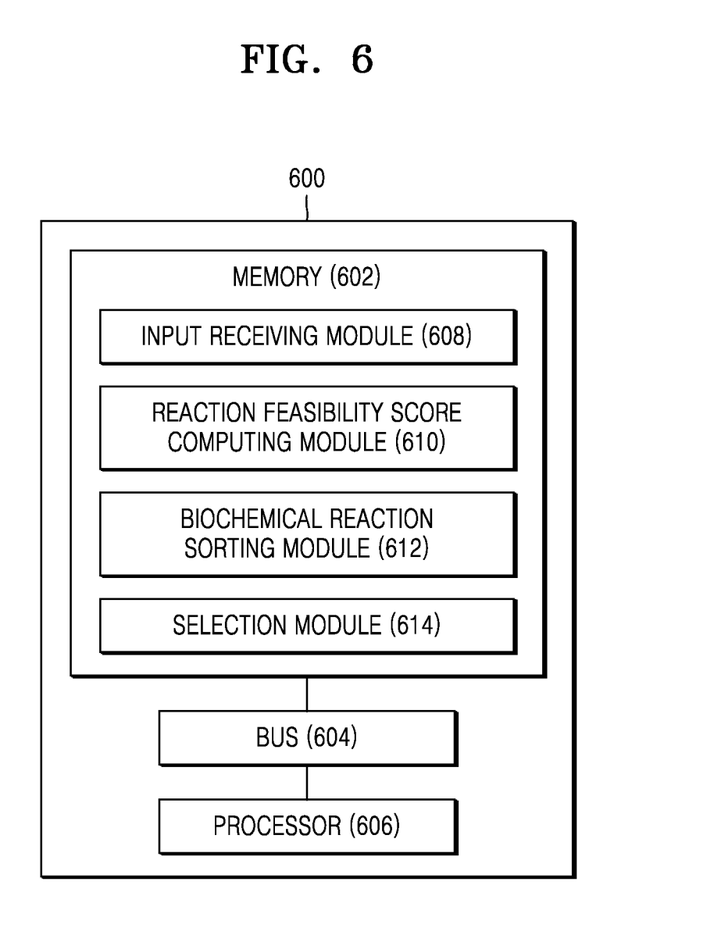
FIG. 6 is a block diagram of a device for assessing a feasibility of a biochemical reaction in an organism, according to an example embodiment.

The knowledge base includes data regarding substrates and/or enzymes corresponding to a set of reactions, one or more transformations corresponding to the set of reactions, the probability of occurrence of transformations reported in the organism and/or other biochemical sources, and/or a list of biochemical catalysts. The knowledge base may include a database system directly or remotely connected with a system or device (e.g., device 600 of FIG. 6) implementing methods of the present embodiments.

Figure 1:
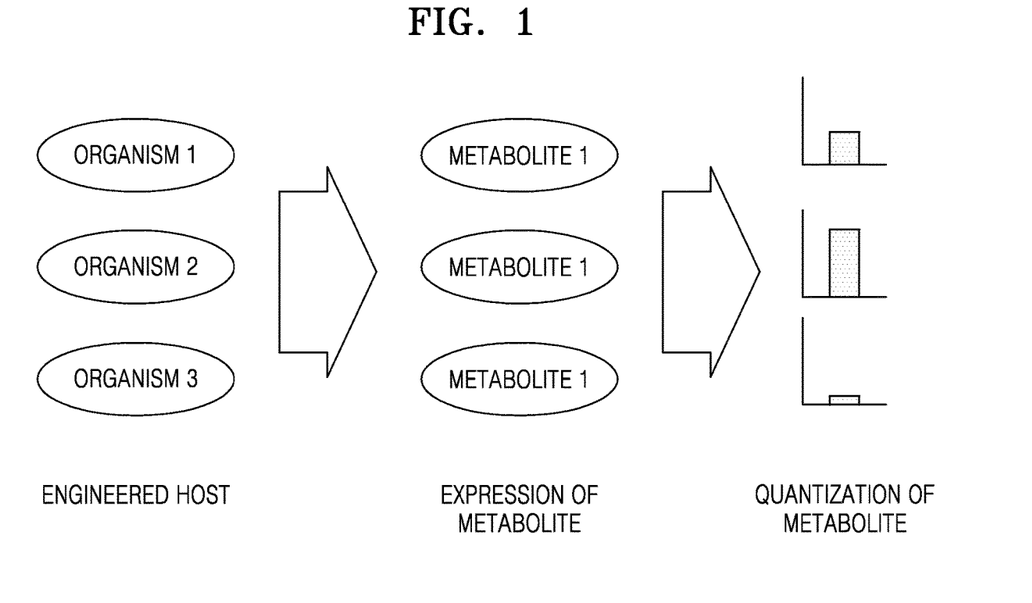
FIG. 1 is a schematic representation of a metabolite reported in different concentrations across organisms, according to an example embodiment.

FIG. 1 is a schematic representation of a metabolite reported in different concentrations across organisms, according to an example embodiment.

Referring to FIG. 1, the engineering efficiency may be determined based on a difference in concentration of a metabolite across various organisms. Thus, it may be important to select a proper host for engineering, for the success of the process.

Figure 2:
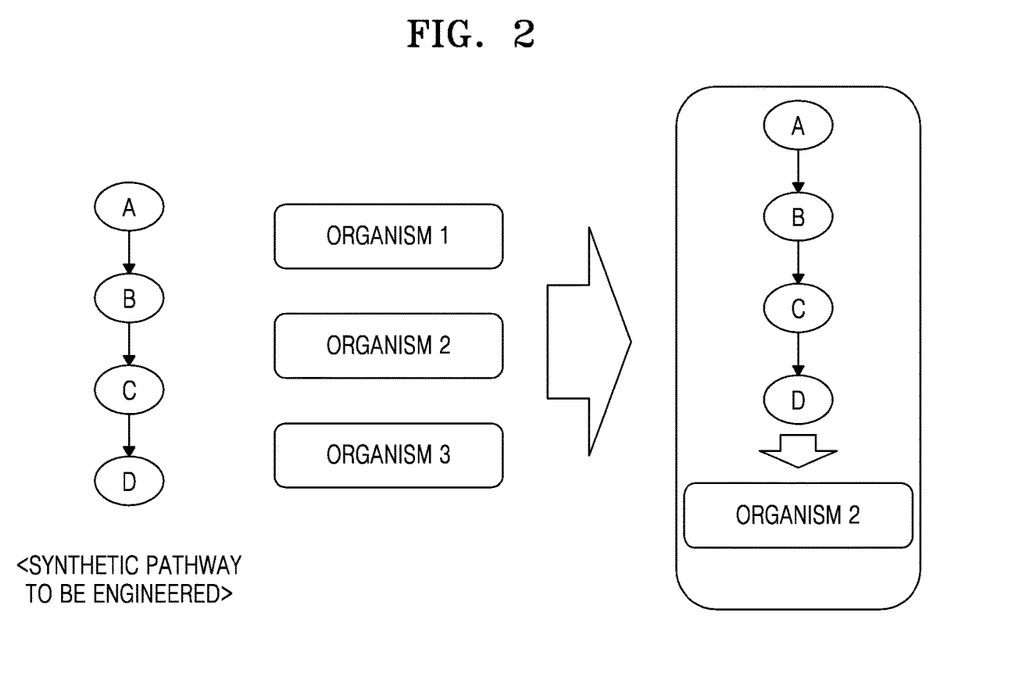
FIG. 2 is a schematic representation of selection of an organism most suitable for a pathway to be engineered, according to an example embodiment.

FIG. 2 is a schematic representation of selection of an organism most suitable for a pathway to be engineered, according to an example embodiment.

Referring to FIG. 2, for the best solution, it is necessary to screen various microorganisms and to select a host organism based on objective functions. The host organism may be selected based on maximization of a yield rate of a target material, stability of an organism, and other environmental parameters. In general, specialized industrial variations may have standardized parameters later. Thus, it is important to assess a reaction to be engineered in a given organism, based on biochemical processing. It may be difficult, or in most cases, may be experimentally impossible to engineer the reaction and identify all potential hosts. Analyzing and ranking of hosts by a computer makes it possible to select an organism to be engineered, which may make exhaustive experimental verification unnecessary.

Unfortunately, current selection of hosts/reactions is primarily performed based on host enzyme capacities for catalyzing engineered reactions. However, currently, the feasibility of the engineered reactions of an organism is not considered.

In view of the foregoing, there is a need for a method of assessing a feasibility of a biochemical reaction in an organism, which is fast, efficient, and accurate.

Figure 3:
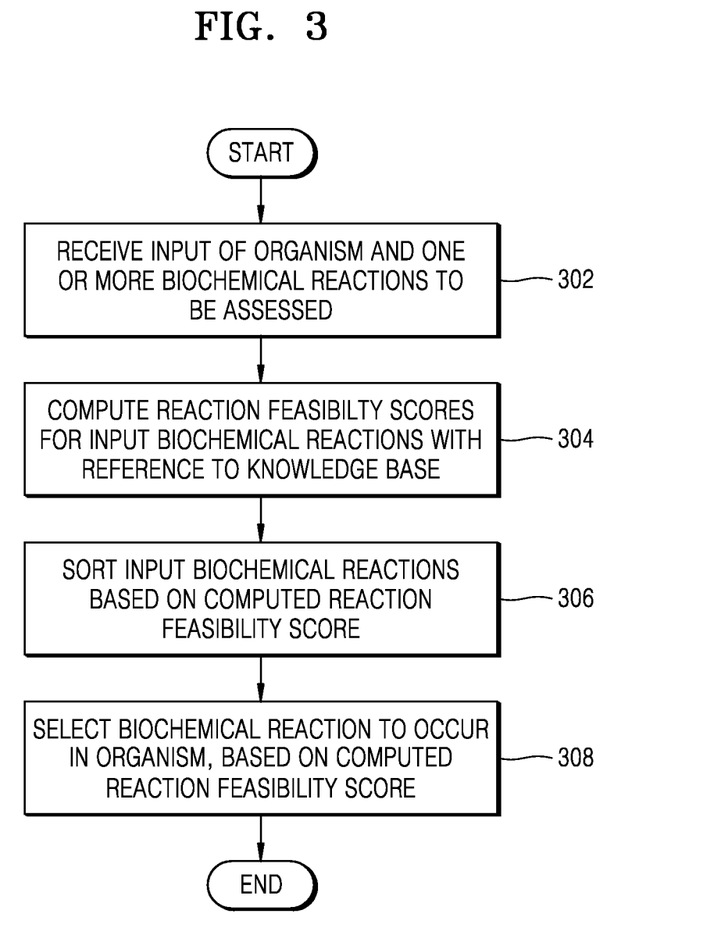
FIG. 3 is a flowchart of a method of assessing a feasibility of a biochemical reaction in an organism, according to an example embodiment.

FIG. 3 is a flowchart of a method of assessing a feasibility of a biochemical reaction in an organism, according to an example embodiment.

An input of the biochemical reaction to be assessed and an input of the organism are received in operation S302. The input of the biochemical reaction may include data or information about transformation(s), a transformation rule governing the transformation, one or more enzymes, and one or more substrates. The input of the organism may include data or information associated with the organism or a name of the organism. When information associated with the organism is not input, the information associated with the organism may be retrieved or fetched from a knowledge base for further processing. The information associated with the organism may include a list of reactions carried out in the organism, transformation(s) taking place in the organism and a related transformation rule, and enzymes, substrates and reactions associated with the organism.

In operation S304, a reaction feasibility score of the biochemical reaction is computed based on the knowledge base. The reaction feasibility score may be computed based on a similarity score (n), a transformation score ($t_s$), or a combination thereof. The reaction feasibility score may include an index indicating the possibility that a given biochemical reaction, such as synthesis or degradation of chemicals, is carried out in the organism. The similarity score accesses a similarity of reactions/substrates from the reaction that is to be engineered in the organism, or a similarity of a set of reactions from a biochemical source. The similarity score for the biochemical reaction may be computed based on a parameter indicating a similarity distance between a reference reaction available in the knowledge base and the biochemical reaction including all participating substrates taking part in the biochemical reaction. The reaction selected as the reference reaction from the knowledge base may be the reaction that is closest to the input biochemical reaction. The similarity score estimates the likelihood of the participating substrates adapting in a host organism. For example, the similarity score may be obtained by mathematically computing an average similarity of all substrates, with respect to all the known substrates within a selected organism or a set of reactions from a biochemical source.

The transformation score for the biochemical reaction may be computed based on a parameter indicating a probability of the transformation, based on the knowledge base. The transformation score assesses the feasibility of the chemical transformation to be performed by the organism, based on the probability of occurrence of the transformation associated with the biochemical reaction, with reference to the knowledge base. The probability of the transformation of the biochemical reaction may be obtained by comparing the probability of the transformation of the biochemical reaction with a probability of occurrence of similar transformation that is present in the knowledge base.

When the list of biochemical catalysts is provided from the knowledge base, the substrate corresponding to an associated reaction, transformation corresponding to the associated reaction, and the probability of occurrence of the transformation may be obtained.

Further, the transformation associated with all reactions may be obtained from the list of biochemical catalysts or the set of the reactions that are present in the knowledge base.

The reaction feasibility score is computed by a mathematical function combining the similarity scores and the transformation scores.

According to an example embodiment, the reaction feasibility score may be computed using the following Equation 1.

$$\text{Reaction feasibility}(R_f) = f(n, t_s) \qquad \text{[Equation 1]}$$

Referring to Equation 1, n is the similarity score, that is, an estimate of the reaction/substrate similarity towards a given host, and $t_s$ is the transformation score, that is, an estimate of the feasibility of transformation within the host.

A specific realization of the reaction feasibility function may be a weighted average of the similarity score and the transformation score, as shown in the following Equation 2.

$$R_f = (a*n + b*t_s)/(a+b) \qquad \text{[Equation 2]}$$

Referring to Equation 2, a and b are weighing coefficients.

However, the reaction feasibility function is not limited thereto, and may also be computed through other mathematical formulations, such as geometric averaging, harmonic averaging, etc.

According to an example embodiment, the similarity score may be computed based on a two-dimensional (2D) fingerprint representing the same substrates. The presence or absence of the fingerprint may be represented as bits scores (0, 1). Each substrate within an organism and a substrate associated with the biochemical reaction that is to be assessed may be represented as bit fingerprints, and the bit fingerprints may be compared through a substrate similarity metric, such as a Tanimoto coefficient, as shown in the following Equation 3.

$$n = (\Sigma m_s^{a,b})/(p_n + u_n) \qquad \text{[Equation 3]}$$

Referring to Equation 3, $m_s^{a,b}$ is the substrate similarity computed between substrate a and substrate b, and $p_n$ and $u_n$ are the number of pairs and unpaired substrates, respectively.

The transformation score computes a propensity of the transformation that is to be performed within an organism or a set of reactions from a biochemical source. The propensity may be estimated by assessing all the known biochemical reactions within an organism which hasn't been studied much, grouping the reactions having the same transformation nature, and assessing the relative frequency in which particular transformation occurs. According to an embodiment, the transformation score $t_s$ may be computed by using the following Equation 4.

$$t_s = p_a/p_m \qquad \text{[Equation 4]}$$

Figure 4:
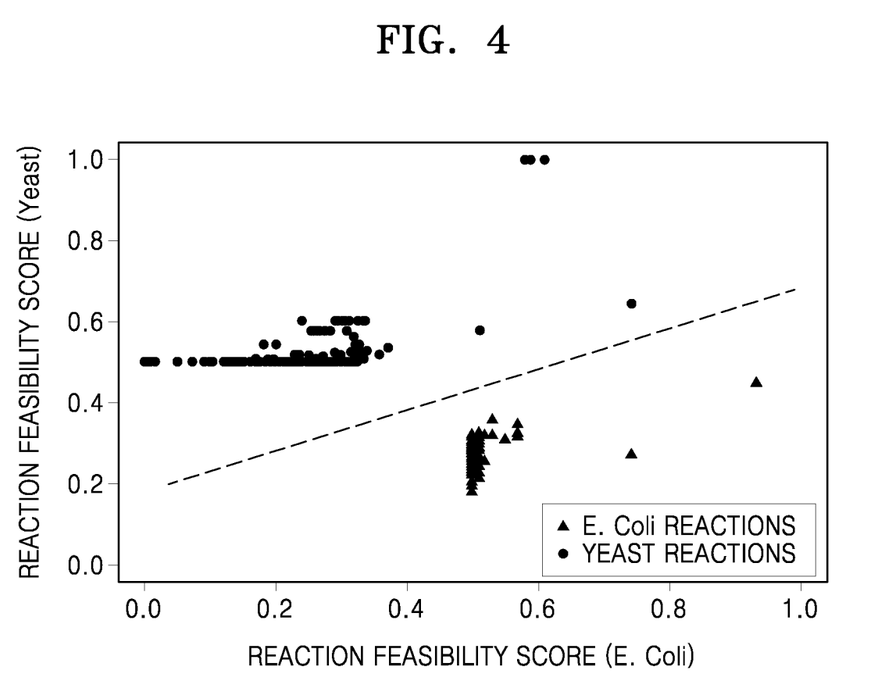
FIG. 4 is a graph representing reaction feasibility scores of individual reactions in *Escherichia coli* and *Saccharomyces cerevisiae*, according to an example embodiment.

Referring to FIG. 4, $t_s$ is the transformation score of a given organism, and $p_a$ is a probability of transformation occurring in the organism. $p_m$ is a probability of the most frequent transformation occurring in the organism, and is used for scaling, which is to take care of incomplete data.

However, the transformation score function of Equation 4 is not limited thereto, and may also be computed through other mathematical formulations, such as odd-score, log-odd score, probability based on a pair of transformations (joint probability or conditional probability), etc.

Once the similarity score and the transformation score of the reaction are obtained, the reaction feasibility score is computed according to Equation 1 described above.

The input reaction may be a single reaction or multiple reactions arranged in a sequential manner to form a reaction pathway. Therefore, when the input includes a biochemical reaction pathway, once reaction feasibilities for individual reactions forming the reaction pathway are computed, the pathway feasibility score for the whole pathway may be computed based on the reaction feasibilities for the individual reactions. According to an embodiment, the pathway feasibility score may be computed using the following Equation 5.

$$\text{Pathway feasibility}(P_f) = \Sigma R_f/N \qquad \text{[Equation 5]}$$

The pathway feasibility is an arithmetic mean of reaction feasibility scores of all the reactions in the pathway.

The pathway feasibility is not limited thereto and may also be computed through other mathematical formulations, such as geometric averaging, harmonic averaging, etc.

In operation S306, the input biochemical reactions are sorted based on the computed reaction feasibility score. Alternatively, when the input data includes biochemical reaction pathways, the biochemical reaction pathways may be sorted based on the pathway feasibility score.

In operation S308, a biochemical reaction is selected based on the computed feasibility score of the reactions that may occur in the organism. Here, the biochemical reaction having the reaction feasibility score that is equal to or greater than a preset threshold score is selected. Alternatively, when the input includes the biochemical reaction pathways, the biochemical reaction pathways may be selected based on the pathway feasibility score.

Further, the selected biochemical reactions may be ranked based on a preset criterion and the biochemical reaction having the highest rank may be selected. The preset criterion may be a reaction feasibility threshold score that is set by a user.

When the reaction feasibility score for the input biochemical reactions is computed, it may be possible to determine the most suitable organism in which the biochemical reaction may occur successfully, from a list of the input organisms, based on the computed reaction feasibility score.

According to another embodiment, an organism for engineering the selected biochemical reaction may be selected from among the input organisms, based on the computed reaction feasibility score.

FIG. 4 is a graph representing reaction feasibility scores of individual reactions in *Escherichia coli* and *Saccharomyces cerevisiae*, according to an embodiment.

619 unique reactions from *Escherichia coli* and *Saccharomyces cerevisiae* were considered to assess whether a reaction may occur in other of the organisms. Referring to FIG. 4, reactions always scored higher for their native organism compared to other organisms and a perfect bi-partition of the data was possible. This indicates the robustness and applicability of the method of the present embodiment, across different reactions.

Figure 5A:
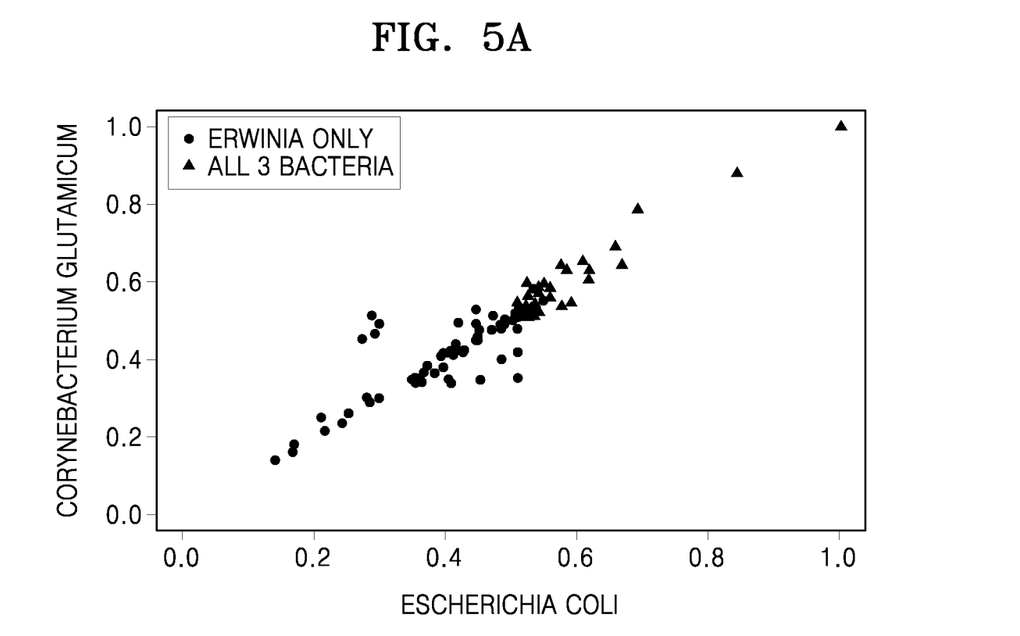
FIGS. 5A and 5B are graphs representing reaction feasibility scores of *Escherichia coli* reactions in *Erwinia oleae* and *Corynebacterium glutamicum*, according to an example embodiment.
Figure 5B:
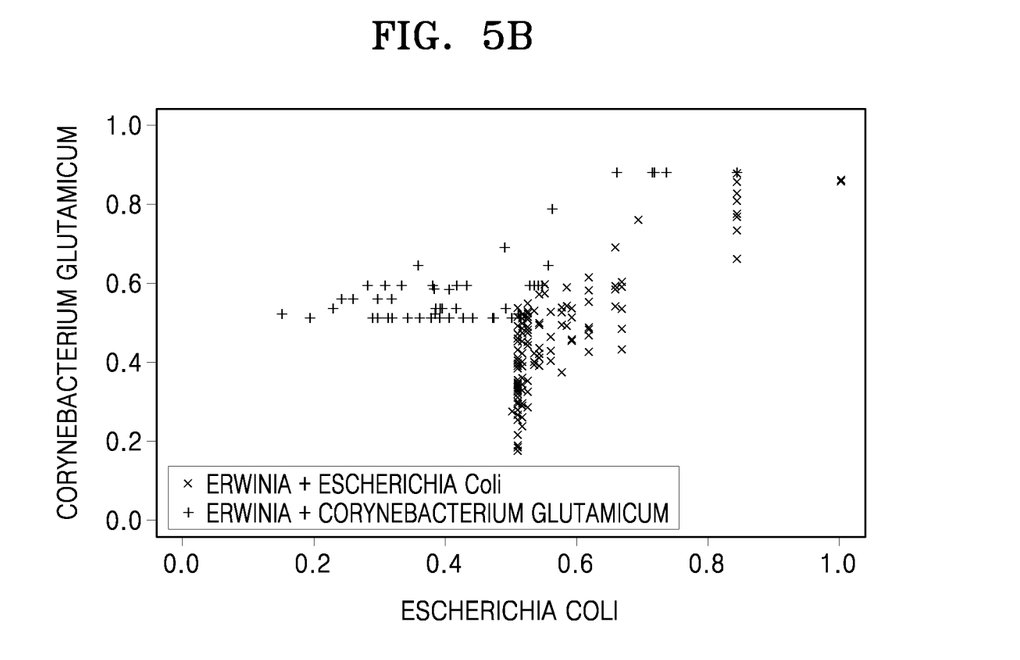

FIGS. 5A and 5B are graphs representing reaction feasibility scores of *Escherichia coli* reactions in *Erwinia oleae* and *Corynebacterium glutamicum*, according to an embodiment.

FIGS. 5A and 5B show assessed feasibilities of *Escherichia coli* (taxonomic family: Enterobacteriaceae) biochemical reactions across *Erwinia oleae* (taxonomic family: Enterobacteriaceae) and *Corynebacterium glutamicum* (taxonomic family: Corynebacteriaceae).

735 reactions from *Escherichia coli* were obtained from Metacyc, and the reactions were assessed for their presence in *Erwinia oleae* and *Corynebacterium glutamicum*. Based on the method according to the present embodiment, plotting of the reaction feasibility score for each of the *Erwinia oleae* was assessed in *Escherichia coli* and *Corynebacterium glutamicum*.

Data distributions shown in FIGS. 5A and 5B are presented in Table 1 below.

TABLE 1

| Data Distribution | |
|---|---|
| Only *Erwinia oleae* | 84 |
| All 3 bacteria | 377 |
| *Erwinia oleae* and *E. coli* | 153 |
| *Erwinia oleae* and *Corynebacterium* | 62 |

Referring to circular points of FIG. 5A, reactions exclusively reported in *Erwinia oleae* have a low feasibility in both *E. coli* and *Corynebacterium glutamicum*. On the contrary, referring to triangular points of FIG. 5A, reactions reported in all three bacteria have feasibility scores that are equal to or higher than 0.5.

Referring to the "x" points of FIG. 5B, reactions shared between *Erwinia oleae* and *E. coli* have a higher feasibility in *E. coli* compared to *Corynebacterium glutamicum*, and referring to the "+" points of FIG. 5B, reactions shared between *Erwinia oleae* and *Corynebacterium glutamicum* have a higher feasibility in *Corynebacterium glutamicum* compared to *E. coli*.

FIG. 6 is a block diagram of a device 600 for assessing a feasibility of a biochemical reaction in an organism, according to an example embodiment.

The device 600 may include a processor 606, and a memory 602 connected to the processor 606, e.g., via a bus 604.

The processor 606 may be realized as any type or types of computational circuits. For example, the processor 606 may include a microprocessor, a microcontroller, a complex instruction set computing (CISC) microprocessor, a reduced instruction set computing (RISC) microprocessor, a very long instruction word (VLIW) microprocessor, an explicitly parallel instruction computing microprocessor (EPIC), a digital signal processor (DSP), any other types of processing circuit, or a combination thereof.

The memory 602 may include a plurality of modules stored in the form of an executable program which instructs the processor 606 to perform the operations illustrated in FIG. 3. The memory 602 may include an input receiving module 608, a reaction feasibility score computing module 610, a biochemical reaction sorting module 612, and a selection module 614.

Computer memory elements may include any suitable memory devices for storing data and executable programs, such as read only memory (ROM), random access memory (RAM), erasable programmable read only memory (EPROM), electrically erasable programmable read only memory (EEPROM), a hard drive, a removable media drive for handling memory cards, and the like. The embodiments of the present disclosure may be implemented in conjunction with program modules, may include functions, procedures, data structures, and application programs, may perform tasks, or may define abstract data types (ADT) or low-level hardware contexts. Executable programs stored in any of the above-mentioned storage media may be executed by the processor 606.

The input receiving module 608 may instruct the processor 606 to perform the operation S302 of FIG. 3.

The reaction feasibility score computing module 610 may instruct the processor 606 to perform the operation S304 of FIG. 3.

The biochemical reaction sorting module 612 may instruct the processor 606 to perform the operation S308 of FIG. 3.

The selection module 614 may instruct the processor 606 to perform the operation S310 of FIG. 3.

According to another embodiment, the selection module 614 may instruct the processor 606 to perform ranking of selected biochemical reactions based on a preset criterion and to select a biochemical reaction having the highest rank.

According to another embodiment, the selection module 614 may instruct the processor 606 to select an organism in which the selected biochemical reaction is to occur, out of multiple input organisms, based on a computed reaction feasibility score, and rank the selected organism based on the computed reaction feasibility score.

The device described herein may comprise a processor, a memory for storing program data and executing it, a permanent storage such as a disk drive, a communication port for handling communication with external devices, and user interface devices, etc. Any processes may be implemented as software modules or algorithms, and may be stored as program instructions or computer-readable codes executable by a processor on a computer-readable recording medium such as read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. This media can be read by the computer, stored in the memory, and executed by the processor.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the present invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the inventive concept and are not intended to otherwise limit the scope of the inventive concept in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those of ordinary skill in this art without departing from the spirit and scope of the present invention.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method for engineering a selected biochemical reaction, the method comprising:
   assessing a feasibility of one or more input biochemical reactions for each of a plurality of input organisms;
   selecting an organism for engineering the selected biochemical reaction from among the plurality of input organisms based on the feasibility of the one or more input biochemical reactions in each of the input organisms, wherein assessing the feasibility of the one or more input biochemical reactions for each of the plurality of input organisms comprises the steps, implemented in a processor, of:
      receiving an input representing each of the input organisms and an input representing one or more biochemical reactions that are to be assessed;
      computing a reaction feasibility score for each of the one or more biochemical reactions of each of the input organisms with respect to a knowledge base, each respective reaction feasibility score computed as a function of a similarity score and a transformation score, the similarity score computed using a two-dimensional fingerprint where the presence or absence of a substrate fingerprint is represented as a bit score; and
      selecting the biochemical reaction that is most likely to occur in each of the input organisms, based on the computed reaction feasibility score thereof; and
   completing the selected biochemical reaction using the selected organism.

2. The method of claim 1, wherein the reaction feasibility score is an index indicating a feasibility that a biochemical reaction is carried out in the organism, wherein the biochemical reaction is synthesis or degradation of a compound.

3. The method of claim 2, wherein the reaction feasibility score is computed based on a weighted average of the similarity score and the transformation score of each of the one or more biochemical reactions.

4. The method of claim 3, wherein the similarity score is computed based on a parameter indicating a similarity distance between a reference reaction available in the knowledge base and the selected biochemical reaction.

5. The method of claim 3, wherein the transformation score is computed based on a parameter indicating a transformation probability of transformations to occur, based on the knowledge base.

6. The method of claim 1, wherein the knowledge base comprises information of one or more substrates corresponding to a set of the one or more biochemical reactions, one or more transformations corresponding to the set of the one or more biochemical reactions, a probability of occurrence of transformations reported in organisms or other biochemical sources, and a list of biochemical catalysts.

7. The method of claim 1, wherein the selecting of the biochemical reaction comprises selecting the biochemical reaction of which the computed reaction feasibility score is equal to or greater than a pre-set threshold score, from among the one or more biochemical reactions.

8. The method of claim 1, wherein the selecting the biochemical reaction includes sorting the one or more biochemical reactions, based on the computed reaction feasibility score, and selecting the biochemical reaction having a highest rank.

9. A non-transitory computer-readable recording medium having recorded thereon a computer program for executing the method of:
   receiving an input representing input organisms and an input representing one or more biochemical reactions in each of the input organisms that are to be assessed;
   computing a reaction feasibility score for each of the one or more biochemical reactions in each of the input organisms with respect to a knowledge base, each respective reaction feasibility score computed as a function of a similarity score and a transformation score, the similarity score computed using a two-dimensional fingerprint where the presence or absence of a substrate fingerprint is represented as a bit score;
   sorting the one or more biochemical reactions, based on the computed reaction feasibility score;
   selecting the biochemical reaction that is most likely to occur in each of the input organisms, based on the computed reaction feasibility score;
   selecting an organism for engineering a selected biochemical reaction from among the input organisms based on the feasibility of the one or more input biochemical reactions in each of the input organisms; and
   causing the selected biochemical reaction to be completed using the selected organism.

10. A device for engineering a selected biochemical reaction, the device comprising:

a processor configured to assess a feasibility of one or more biochemical reactions for each of a plurality of input organisms and to select an organism for engineering the selected biochemical reaction from among the plurality of input organisms based on the feasibility of the one or more input biochemical reactions in each of the input organisms, wherein the processor receives an input representing the organism and an input representing one or more biochemical reactions that are to be assessed, computes a reaction feasibility score for each of the one or more biochemical reactions with respect to a knowledge base, each respective reaction feasibility score computed as a function of a similarity score and a transformation score, the similarity score computed using a two-dimensional fingerprint where the presence or absence of a substrate fingerprint is represented as a bit score, sorts the one or more biochemical reactions based on the computed reaction feasibility score, selects the biochemical reaction that is most likely to occur in the organism, based on the computed reaction feasibility score, and causes the selected biochemical reaction to be completed using the selected organism; and a memory connected to the processor.

11. The device of claim 10, wherein the reaction feasibility score is an index indicating a feasibility that a biochemical reaction is carried out in the organism, wherein the biochemical reaction is synthesis or degradation of a compound, and the reaction feasibility score is computed based on a weighted average of the similarity score and the transformation score of each of the one or more biochemical reactions.

12. The device of claim 11, wherein the similarity score is computed based on a parameter indicating a similarity distance between a reference reaction available in the knowledge base and the biochemical reaction, and the transformation score is computed based on a parameter indicating a transformation probability of transformations to occur, based on the knowledge base.

13. The device of claim 10, wherein the knowledge base comprises information of one or more substrates corresponding to a set of the one or more biochemical reactions, one or more transformations corresponding to the set of the one or more biochemical reactions, a probability of occurrence of transformations reported in organisms or other biochemical sources, and a list of biochemical catalysts.

14. The device of claim 10, wherein the processor is configured to select the biochemical reaction of which the computed reaction feasibility score is equal to or greater than a pre-set threshold score, from among the one or more biochemical reactions.

* * * * *